(12) United States Patent
Kaercher et al.

(10) Patent No.: US 10,492,770 B2
(45) Date of Patent: Dec. 3, 2019

(54) MEDICAL INSTRUMENTS WITH BENDABLE SHAFT

(71) Applicant: Karl Storz SE & Co. KG, Tuttlingen (DE)

(72) Inventors: Daniel Kaercher, Radolfzell (DE); Jochen Stefan, Wald (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 1071 days.

(21) Appl. No.: 13/865,743

(22) Filed: Apr. 18, 2013

(65) Prior Publication Data

US 2013/0304083 A1   Nov. 14, 2013

(30) Foreign Application Priority Data

Apr. 18, 2012   (DE) .................. 10 2012 007 645

(51) Int. Cl.
*A61B 17/00* (2006.01)
*A61B 17/29* (2006.01)
*A61B 90/00* (2016.01)

(52) U.S. Cl.
CPC ........ *A61B 17/00234* (2013.01); *A61B 17/00* (2013.01); *A61B 17/29* (2013.01); *A61B 17/2909* (2013.01); *A61B 2017/0046* (2013.01); *A61B 2017/00473* (2013.01); *A61B 2017/00477* (2013.01); *A61B 2017/291* (2013.01); *A61B 2017/2919* (2013.01);
(Continued)

(58) Field of Classification Search
CPC ... A61B 17/00234; A61B 17/00; A61B 17/29; A61B 17/2909; A61B 2017/0046; A61B 2017/2931; A61B 2017/00477; A61B 2017/2939; A61B 2017/2946; A61B 2017/2927; A61B 2017/291; A61B 2017/00473; A61B 2017/2919; A61B 2019/4868; A61B 1/008; A61B 1/005; A61B 1/01; A61B 1/0051; A61B 2017/2905; A61B 2017/2908; A61B 2017/2934; A61B 2017/2933; A61B 2017/2936
See application file for complete search history.

(56) References Cited

U.S. PATENT DOCUMENTS 5,282,800 A   2/1994   Foshee et al.
5,549,637 A   8/1996   Crainich
(Continued)

FOREIGN PATENT DOCUMENTS

DE   202007003114 U1   6/2007
DE      69836436 T2   9/2007
(Continued)

*Primary Examiner* — Christopher L Templeton
(74) *Attorney, Agent, or Firm* — Whitmyer IP Group LLC (57) ABSTRACT

An articulation device for a medical instrument includes a coupling for releasable mechanical connection of the articulation device to a tool or to the distal end of a shaft, a locking device on the coupling for locking the mechanical connection, and an articulation, which enables the coupling to be angled relative to an end of the articulation device remote from the coupling. The locking device is designed such that the mechanical connection is locked in a predetermined working angular position of the articulation and is releasable in a predetermined release angular position of the articulation.

20 Claims, 4 Drawing Sheets

(52) U.S. Cl.
CPC .......... *A61B 2017/2927* (2013.01); *A61B 2017/2931* (2013.01); *A61B 2017/2939* (2013.01); *A61B 2017/2946* (2013.01); *A61B 2090/0813* (2016.02)

(56) References Cited

U.S. PATENT DOCUMENTS

| | | | |
|---|---|---|---|
| 5,700,276 A * | 12/1997 | Benecke | A61B 17/1608 606/206 |
| 6,673,092 B1 * | 1/2004 | Bacher | A61B 17/2909 606/205 |
| 7,316,703 B2 * | 1/2008 | Suzuki | A61B 17/29 606/208 |
| 8,011,848 B2 | 9/2011 | Sockman et al. | |
| 8,114,017 B2 * | 2/2012 | Bacher | A61B 17/0218 600/204 |
| 8,784,404 B2 * | 7/2014 | Doyle | A61B 34/30 606/1 |
| 8,864,010 B2 * | 10/2014 | Williams | A61B 17/07207 227/175.1 |
| 9,161,772 B2 * | 10/2015 | Hyodo | B25J 13/02 |
| 2006/0190029 A1 * | 8/2006 | Wales | A61B 17/00234 606/205 |
| 2008/0308604 A1 * | 12/2008 | Timm | A61B 17/07207 227/175.1 |
| 2011/0264079 A1 * | 10/2011 | Doll | A61B 17/4241 606/1 |

FOREIGN PATENT DOCUMENTS

| | | |
|---|---|---|
| DE | 102006038516 A1 | 2/2008 |
| DE | 19780579 B4 | 4/2008 |
| EP | 1889579 A2 | 2/2008 |
| WO | 2011056458 A1 | 5/2001 |

* cited by examiner

MEDICAL INSTRUMENTS WITH BENDABLE SHAFT

FIELD OF THE INVENTION

The present invention is directed to a medical instrument with a bendable shaft and to an articulation device for a medical instrument.

BACKGROUND OF THE INVENTION

Medical instruments, in particular microinvasive surgical instruments, have a growing number of degrees of freedom. This allows medical staff to carry out increasingly complex activities and increasing numbers of different activities using a single instrument. For example, in the case of a needle holder or another gripping or cutting tool at the distal end of a long, thin shaft, the option to bend the tool relative to the shaft is desirable for some applications. A possibility of bending or pivoting the tool about an axis perpendicular with respect to the longitudinal axis of the shaft can enable gripping or cutting in a direction that otherwise cannot be reached.

In the case of reusable medical instruments, the possibility of disassembling the tool as extensively as possible as a prerequisite for thorough cleaning is of particular importance. To this end, screw threads or bayonet closures can be used, which are generally locked in a suitable manner. Conventional concepts however cannot be transferred to a medical instrument with a bendable shaft or cannot be easily transferred.

SUMMARY OF THE INVENTION

The object of the present invention is to create an improved articulation device for a medical instrument and an improved medical instrument.

This object is achieved by the subjects of the independent claims.

Developments are disclosed in the dependent claims.

Exemplary embodiments of the present invention are based on the concept of forming a locking device on a coupling in the vicinity of an articulation of a medical instrument, such that a mechanical connection by means of the coupling is locked or releasable according to the angular position of the articulation. The variants and exemplary embodiments described hereinafter show that a locking of the coupling in accordance with the angular position of the articulation can be implemented easily in terms of design and manufacture, and here can enable simple handling at the same time.

A medical instrument comprises a shaft, a coupling at the distal end of the shaft for releasable mechanical connection of a tool to the distal end of the shaft, an articulation proximally of the distal end of the shaft for bending the distal end of the shaft into an adjustable angular position, and a locking device on the coupling for locking a mechanical connection of a tool to the distal end of the shaft, wherein the locking device is designed such that the mechanical connection is locked at a predetermined working angular position of the articulation and is releasable at a predetermined release angular position of the articulation.

An articulation device for a medical instrument comprises a coupling for releasable mechanical connection of the articulation device to a tool or to the distal end of a shaft, a locking device on the coupling for locking the mechanical connection, and an articulation, which enables the coupling to be angled relative to an end of the articulation device remote from the coupling, wherein the locking device is designed such that the mechanical connection is locked at a predetermined working angular position of the articulation and is releasable at a predetermined release angular position of the articulation.

The medical instrument is in particular a microinvasive surgical instrument with a long, thin, straight or curved, rigid or flexible shaft. At the proximal end of the shaft, a handling device in particular is provided, which is designed to receive manually generated forces and torques. The shaft is designed to transfer forces and torques from the handling device to the articulation and to a tool at the distal end of the medical instrument. To this end, the shaft in particular comprises an outer shaft, an inner shaft and/or a transfer rod and/or other transfer devices. Each individual transfer device can be rigid or flexible and can be designed to transfer a force and/or a torque. In particular, at least one transfer device is coupled to the articulation in order to transfer from the handling device to the articulation a force or a torque to adjust the angular position.

The coupling is in particular designed for releasable rigid mechanical connection to a tool. The coupling is designed for example as a screw thread or as a bayonet coupling. The articulation device is connected rigidly and permanently or non-releasably in particular to the distal end of an outer shaft or comprises a further coupling (shaft coupling) for releasable and in particular rigid mechanical connection to a distal end of an outer shaft.

Alternatively, the coupling is designed for releasable rigid mechanical connection to a distal end of a shaft (shaft coupling). The coupling is designed for example as a screw thread or as a bayonet coupling. The articulation device is rigidly and permanently or non-releasably connected in particular to the proximal end of a tool or of a further shaft portion or comprises a further coupling (tool coupling) for releasable and in particular rigid mechanical connection to a proximal end of a tool or of a further shaft portion.

The articulation is designed to enable bending or pivoting about a pivot axis, which is not parallel with respect to the longitudinal axis of the shaft and in particular is perpendicular or substantially perpendicular (angle of at least 60 degrees, in particular at least 80 degrees) with respect to the longitudinal axis of the shaft. The articulation can be designed so as to enable bending merely in a single direction or in a single plane or in two directions perpendicular with respect to one another.

The pivot axis of the articulation may lie within the cross section of the articulation device and for example may be defined by a shaft or journal. Alternatively, the pivot axis may lie outside the contour of the articulation device or may not intersect said contour and may be defined by centers of curvature of sliding surfaces. Furthermore, the articulation can be designed as a linkage, wherein the pivot axis may be dependent on the angular position. Alternatively, the articulation may be designed as a resilient region of a shaft portion, wherein the resilience can be based on the resilience of a component and/or on a plurality of individual articulations arranged in succession.

The articulation and coupling may be arranged directly adjacent to one another, that is to say as closely as allowed by the design. Alternatively, the articulation and coupling are located merely in the vicinity of one another, that is to say they are spaced from one another at a distance, which is small in comparison to the overall dimensions of the medical instrument, for example a tenth of the overall length of the medical instrument. Furthermore, the articulation and coupling may be distanced further from one another.

The locking device can be designed so as to lock the mechanical connection at a plurality of predetermined working angular positions of the articulation, in particular within a working range (in particular a successive working range) of working angular positions. Furthermore, the locking device can be designed such that the mechanical connection is releasable at a plurality of predetermined release angular positions, in particular within a release range (in particular a successive release range) of release angular positions.

The locking and unlocking of a mechanical connection by means of a coupling in accordance with the angular position of an articulation that is coupled to the coupling or to the locking device thereof can enable particularly simple handling when disassembling and assembling a medical instrument. In terms of construction, manufacture and handling, it may be advantageous that no additional actuation device is necessary to unlock the coupling. The variants and exemplary embodiments described here show partly surprisingly simple and robust mechanical solutions.

In the case of a medical instrument or an articulation device as is described here, the locking device is designed in particular such that the mechanical connection is locked in a predetermined working range of working angular positions of the articulation.

For example, the working range comprises working angular positions between 0° (fully straight articulation) and 80° (articulation angled almost at right angles). Release angular positions can adjoin one end or both ends of the working range. A release angular position lies for example at −10° or at a bend of the articulation through 10° in a direction opposite the working angular positions. Alternatively or in addition, a (further) release angular position may lie at the opposite end of the working range, for example at an angle of 90° in the case of the aforementioned example of a working range from 0° to 80°.

In the case of a medical instrument or an articulation device as is described here, the locking device can be designed so as to enable a closing and locking of the mechanical connection even in the working angular position of the articulation.

In particular, a bolt can be provided, which, due to its (for example wedge-shaped or pawl-shaped) design, can also be moved in a working angular position against the force of a spring or another resilient element into an unlocking position, and, when the provided mechanical connection is achieved, returns into its locking position.

In the case of a medical instrument or an articulation device as is described here, the locking device in particular comprises a bolt movable in the axial direction of the coupling, wherein, in a predetermined locking position of the bolt, the mechanical connection is locked, and, in a predetermined unlocking position of the bolt, the mechanical connection is releasable.

The bolt is moved in particular by a spring or by another resilient device into the locking position. The bolt is coupled to the articulation in such a way that the bolt is moved into its unlocking position when the articulation is moved into the release angular position, and in such a way that the bolt adopts its predetermined locking position or one of a number of locking positions when the articulation is located in its working angular position or in one of a number of working angular positions.

In the case of a medical instrument or an articulation device comprising a bolt as is described here, in particular the coupling is a tool coupling for releasable mechanical connection of the articulation device to a tool, and the bolt is arranged and guided on a distal part of the articulation device comprising the coupling, wherein the bolt, in the predetermined release angular position of the articulation, abuts on a proximal part of the articulation device, said proximal part being connected or connectable to a shaft, and is slid by said proximal part into the unlocking position.

An actuation of a bolt, arranged and guided on the distal part of the articulation device, by means of a proximal part of the articulation device can make it possible to lock the coupling in a manner that is particularly simple and robust in terms of design and manufacture. This is true in particular when the pivot axis defined by the articulation lies outside the articulation device.

In the case of a medical instrument or an articulation device as is described here, the coupling is a bayonet coupling in particular and comprises a groove for receiving a catch at a proximal end of a tool.

Alternatively, the coupling may be a bayonet coupling and may comprise a catch, which is provided to be received in a groove at the proximal end of a tool.

The groove is L-shaped in particular with an axial portion (which extends in the axial direction or substantially in the axial direction) and a circumferential portion (which extends in the circumferential direction or substantially in the circumferential direction).

In the case of an articulation device as is described here, the coupling is a tool coupling in particular for releasable mechanical connection of the articulation device to a tool, wherein the articulation device further comprises a shaft coupling for releasable mechanical connection of the articulation device to a shaft, and a shaft locking device, wherein the shaft locking device is designed so as to lock the mechanical connection of the articulation device to a shaft by means of the shaft coupling.

The articulation device may therefore (in particular at opposite ends) comprise a tool coupling for releasable mechanical connection to a tool and a shaft coupling for releasable mechanical connection to a shaft. This can enable extensive disassembly and particularly thorough cleaning of a medical instrument comprising the articulation device.

The shaft locking device is in particular coupled to the articulation in such a way that the shaft coupling is unlocked in a shaft release angular position of the articulation. The release position of the articulation, in which the tool coupling is unlocked, and the shaft release angular position, in which the shaft coupling is unlocked, can be identical, adjacent, abutting one another or distanced from one another. In particular, the release angular position and the shaft release angular position can be arranged at opposite ends of the working range or of the range of the working angular positions. If the release angular position and the shaft release angular position are identical, the tool coupling and the shaft coupling can be unlocked at the same time. If the release angular position and the shaft release angular position are adjacent or abut one another, the tool coupling and the shaft coupling can be unlocked in direct succession. If the release angular position and the shaft release angular position lie at opposite ends of the working range and therefore are distanced far from one another, an accidental unlocking of one of the two couplings can be prevented particularly effectively.

An articulation device comprising a shaft coupling as is described here further comprises in particular a transfer device, which is coupled to the articulation, for transferring a force from the proximal end of a medical instrument to the articulation and for adjusting an angular position of the articulation from the proximal end of the medical instrument, wherein the shaft locking device is coupled to the transfer device.

The transfer device comprises in particular an inner shaft or a transfer rod. The transfer device is in particular displaceable in an outer shaft parallel with respect to the longitudinal axis thereof. In particular, the articulation in a proximal position of the transfer device adopts a straight angular position, and, in a distal position of the transfer device, adopts a angled angular position. The shaft locking device is in particular connected to the transfer device either rigidly or so as to be rotatable merely about the longitudinal axis of the transfer device.

In the case of an articulation device as is described here, in which the coupling is not a tool coupling, the coupling is in particular a shaft coupling for releasable mechanical connection of the articulation device to a shaft, wherein a bolt is arranged and guided on a proximal part of the articulation device comprising the coupling, and wherein the bolt, in the predetermined release angular position of the articulation, abuts on a distal part of the articulation device, said distal part being connected or connectable to a tool, and is slid by the distal part of the articulation device into an unlocking position.

A medical instrument comprises an articulation device as is described here.

The medical instrument in particular further comprises a shaft, of which the distal end is connectable or is connected to the articulation device, and a handling device, which can be releasably mechanically coupled to the proximal end of the shaft, wherein the predetermined release angular position of the articulation cannot be reached when the handling device is coupled to the proximal end of the shaft.

A blocking of the release angular position and, in the case of two couplings, of (identical or different) release angular positions by means of the handling device may make it possible for a medical instrument that can be disassembled into a number of parts to be fully disassembled merely after actuation of an unlocking actuation device on the handling device and release of the shaft from the handling device. This enables particularly simple and quick disassembly of the medical instrument after brief training and can thus reduce the necessary staff costs.

DETAILED DESCRIPTION OF THE INVENTION

Figure 1:
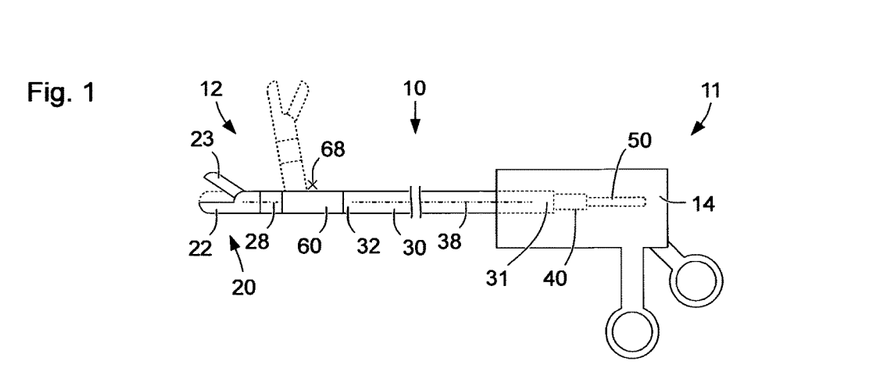
FIG. 1 shows a schematic illustration of a medical instrument.

FIG. 1 shows a schematic illustration of a medical instrument 10 having a proximal end 11 and a distal end 12. The medical instrument 10 comprises at the proximal end 11 a handling device 14 and at the distal end 12 a tool 20. The handling device 14 comprises a plurality of grip parts, which are movable at least in part relative to one another. Furthermore, the handling device 14 may comprise further actuation devices, which are manually movable.

The handling device 14 and the tool 20 are mechanically interconnected by an outer shaft 30 and an articulation device 60. An inner shaft 40 and a transfer rod 50 are arranged concentrically in the outer shaft 30. In FIG. 1, only the proximal ends of the inner shaft 40 and of the transfer rod 50 are indicated. The inner shaft 40 and the transfer rod 50 are displaceable parallel with respect to the longitudinal axis 38 of the outer shaft and/or rotatable about the longitudinal axis 38, in each case independently of one another.

With the concentric arrangement of the outer shaft 30, inner shaft 40 and transfer rod 50, the longitudinal axis 38 of the outer shaft 30 is simultaneously the longitudinal axis of the inner shaft 40 and of the transfer rod. The outer shaft 30, inner shaft 40 and transfer rod 50 may each be rotationally symmetrical about the longitudinal axis 38. If the outer shaft 30 (and with it the inner shaft 40 and transfer rod 50) is curved, by contrast with the illustration in FIG. 1, the longitudinal axis 38 hereinafter means the longitudinal axis of the outer shaft 30 at its distal end 32.

The tool 20 comprises a stationary mouth part 22 and a mouth part 23 pivotable about a pivot axis perpendicular with respect to the drawing plane of FIG. 1. The articulation device 60 enables the entire tool 20 with both mouth parts 22, 23 to pivot about a pivot axis 68 perpendicular with respect to the drawing plane of FIG. 1 as far as a position that is indicated in FIG. 1 in dashed lines. Irrespective of this, that is to say in particular in any angular position of the articulation device 60, the tool 20 is rotatable about its longitudinal axis 28. The longitudinal axis 28 of the tool 20 is parallel with respect to the longitudinal axis 38 of the outer shaft 30 only in the straight angular position of the articulation device 60 illustrated in FIG. 1 in solid lines.

The handling device 14 is designed so as to transfer to the outer shaft 30, the inner shaft 40 and the transfer rod 50 forces and torques generated manually by medical staff or exerted on grip parts or other actuation devices on the handling device 14. In particular, one or more movable grip parts, rotary knobs or other actuation devices on the handling device 14 are coupled to the inner shaft 40 and the transfer rod 50 in such a way that the inner shaft 40 and the transfer rod 50 can be displaced parallel with respect to the longitudinal axis 38 or rotated about the longitudinal axis 38 by means of actuation of the actuation devices.

In FIG. 1, distal ends (not illustrated) of the inner shaft 40 and of the transfer rod 50 are coupled to the tool 20 and the articulation device 60. In the examples presented hereinafter with reference to FIGS. 2 to 13, in particular the inner shaft 40 is coupled to the articulation device 60, and the transfer rod 50 is coupled to the tool 20. As a result of a displacement of the inner shaft 40 parallel with respect to the longitudinal axis 38, the articulation device 60 can be adjusted and the tool 20 can be continuously pivoted between the straight position illustrated in solid lines and the angled position illustrated in dashed lines. By means of a displacement of the transfer rod 50 parallel with respect to the longitudinal axis 38, the pivotable mouth part 23 can be pivoted towards the stationary mouth part 22 and away therefrom. By means of a rotation of the transfer rod 50 about the longitudinal axis 38, the tool 20 can be rotated about the longitudinal axis 28 thereof. The transfer rod 50 is flexible at least in the region of the articulation device 60 and is torsionally rigid over its entire length. If, by contrast to the illustration in FIG. 1, the outer shaft 30 is curved or flexible, the inner shaft 40 and the transfer rod 50 are likewise flexible, in particular at least in the curved or resilient regions of the outer shaft 30.

Exemplary embodiments of the tool 20, of the outer shaft 30 and of the articulation device 60, which may be suitable both for forming the medical instrument 10 presented above with reference to FIG. 1 and for forming a medical instrument having features and properties that deviate from those presented above with reference to FIG. 1, are presented hereinafter with reference to FIGS. 2 to 13.

Figure 2:
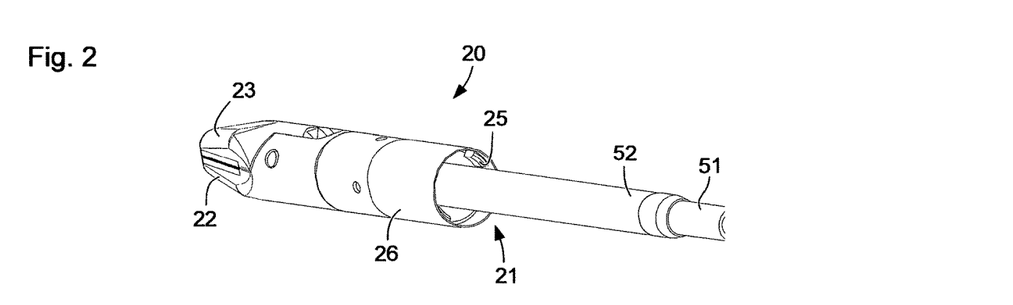
FIG. 2 shows a schematic axonometric illustration of a tool.

FIG. 2 shows a schematic axonometric illustration of a tool 20 comprising a proximal end 21 and distal end, which is formed by a stationary mouth part 22 and a pivotable mouth part 23. The tool 20 comprises at the proximal end 21 two mutually opposed claws or catches 25, which each protrude radially inwardly. The catches 25 form a coupling for releasable mechanical connection of the tool 20 to the distal end of an articulation device 60 (see FIG. 1). At the proximal end 21, the tool 20 comprises a sleeve 26, which, inter alia, surrounds the catches 25 in the manner of a circular sheath.

The tool 20 is connected to the distal end of the transfer rod 50 (see FIG. 1). In FIG. 2, a rigid proximal portion 51 and a resilient distal portion 52 of the transfer rod can be seen. The rigid proximal portion 51 takes up the majority of the length of the transfer rod. The resilient distal portion 52 is provided for arrangement in the region of the articulation device 60 (see FIG. 1). To this end, the resilient distal portion 52 of the transfer rod is flexible, but is rigid for the transfer of tensile and compressive forces in the longitudinal direction and of torques.

The transfer rod, in particular the resilient distal portion 52 thereof, is effectively coupled to the pivotable mouth part 23 of the tool 20 in such a way that a displacement of the transfer rod in the longitudinal direction thereof is coupled with an opening or closing pivoting movement of the pivotable mouth part 23 relative to the stationary mouth part 22. Furthermore, the mouth parts 22, 23 are rotatable relative to the proximal end 21, the catches 25 and the sleeve 26 of the tool 20 about the longitudinal axis 28 (see FIG. 1). A rotation of the transfer rod 51, 52 about its longitudinal axis causes a corresponding rotation of the mouth parts 22, 23.

Figure 3:
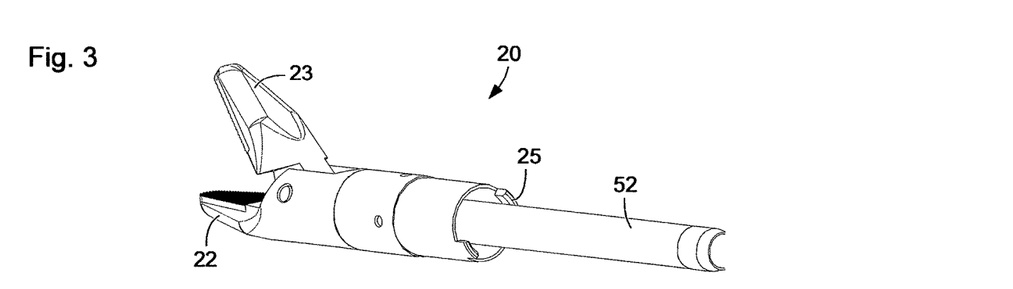
FIG. 3 shows a further schematic axonometric illustration of the tool from FIG. 2.

FIG. 3 shows a further schematic axonometric illustration of the tool 20 from FIG. 2 from a similar perspective or from a similar viewer position. The illustration in FIG. 3 differs from the illustration in FIG. 2 in particular in that the pivotable mouth part 23 is shown in an open or opened position. A further difference between FIGS. 2 and 3 lies in the fact that the sleeve 26 is not shown in FIG. 3. The catches 25 can therefore be seen more clearly.

Figure 4:
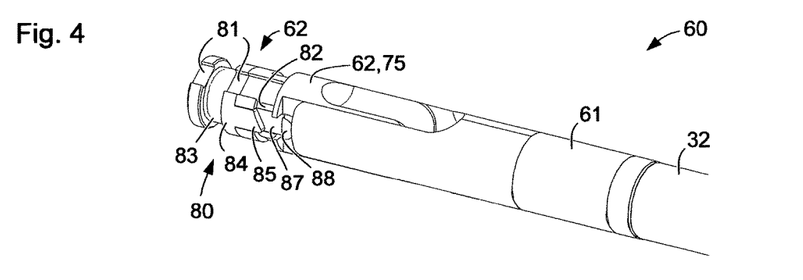
FIG. 4 shows a schematic axonometric illustration of an articulation device.

FIG. 4 shows a schematic axonometric illustration of an articulation device 60 having a proximal part 61 and a distal part 62. As is presented below with reference to FIGS. 5 to 8, the distal part 62 is pivotable about a pivot axis 68 (see FIG. 1) relative to the proximal part 61 of the articulation device. The proximal part 61 of the articulation device 60 is rigidly mechanically connectable in a releasable manner to the distal end 32 of an outer shaft 30. This mechanical coupling is described below with reference to FIGS. 8 to 13.

At the distal end of the distal part 62 of the articulation device 60, a coupling 80 is provided. The coupling 80 comprises two mutually opposed L-shaped grooves, of which only one faces towards the viewer in FIG. 4 and is therefore visible. The L-shaped grooves each have an axial portion 81 and a circumferential portion 82, which are arranged and designed such that each L-shaped groove 81, 82 can receive a catch 25 of the tool 20 (see FIG. 2).

The coupling 80 further comprises an annular slide 84, which is movable in the axial direction and is held by a spring 83 in the position shown in FIG. 4. On the slide 84, two bolts 85 extending proximally in the axial direction are provided, of which only one faces towards the viewer in FIG. 4 and is therefore visible. At its proximal end, the bolt 85 has a triangular or wedge-shaped or pawl-shaped design and protrudes in the position shown in FIG. 4 of the slide 84 into the circumferential portion 82 of the L-shaped groove. The bolt 85 is rigidly connected to a lobe 88 via a thin web 87 arranged at the base of the circumferential portion 82 and outside the cross section of the circumferential portion 82 of the L-shaped groove, and in particular is formed in one piece with said lobe.

The articulation device 60, in particular the distal part 62 thereof, is illustrated in FIG. 4 in a straight working angular position 75, which corresponds to the position of the articulation device and of the tool 20 illustrated in FIG. 1 in solid lines. When the transfer rod 51, 52 connected to the tool 20 is introduced into a central channel (not visible in FIG. 4) in the articulation device 60 and in the shaft, the catches 25 of the tool 20 shown in FIGS. 2 and 3 can be guided from a distal direction in a proximal direction through the axial portions 81 of the L-shaped grooves as far as the circumferential portions 82 thereof. With a subsequent rotational movement of the tool 20 relative to the articulation device 60 and in particular relative to the coupling 80, the catches 25 are moved in the circumferential portions 82 of the L-shaped grooves. Due to the triangular design of the bolts 85, the slide 84 together with the bolts 85 and the lobe 88 is displaced distally against the force of the spring 83 until the catches 25 are moved completely past the bolts 85 and the slide 84 returns with the bolts 85 and the lobe 88 into its position shown in FIG. 4 as a result of the force of the spring 83. The bolts 85 then hold the catches 25 in an interlocked manner in the reached position and thus lock the rigid mechanical connection between the tool 20 and the articulation device 60 or the coupling 80 thereof.

Figure 5:
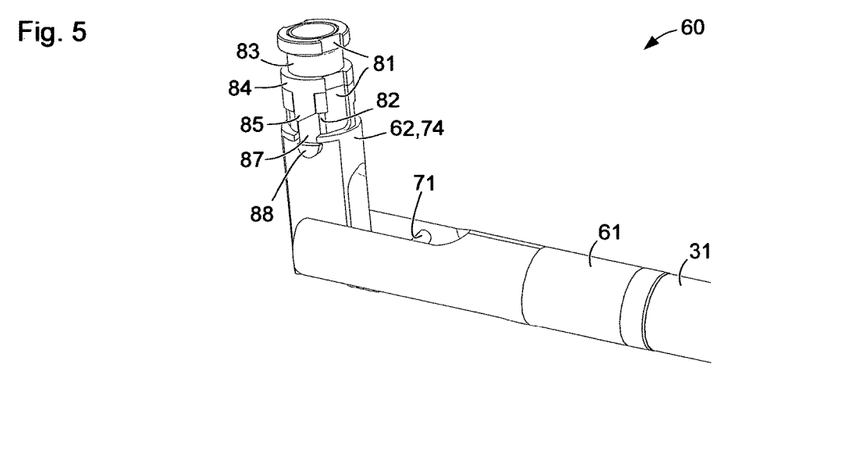
FIG. 5 shows a further schematic axonometric illustration of the articulation device from FIG. 4.

FIG. 5 shows a further schematic axonometric illustration of the articulation device 60 from FIG. 4. The illustration in FIG. 5 differs from the illustration in FIG. 4 in that the articulation device 60, in particular the distal part 62 of the articulation device 60, is shown in an angled working angular position 74, which corresponds approximately to the angular position of the articulation device and of the tool 20 shown in FIG. 1 in dashed lines. On the inner face of the fork-shaped proximal part 61 of the articulation device 60, said inner face being visible in part in FIG. 5, one end of a curved groove 71 can be seen. The groove 71, which in particular is shaped in the manner of a circular arc, together with a web (not visible in FIG. 5) on the distal part 62 of the articulation device 60, said distal part engaging in the groove 71, and together with a further groove and further web, which are arranged in an axially symmetrical manner, forms the actual articulation of the articulation device 60. The centers of curvature of the grooves 71 define the position of the pivot axis 68 (see FIG. 1). In the example illustrated here, the pivot axis 68 is arranged outside the cross section or the contour of the articulation device 60, that is to say the pivot axis 68 does not intersect the articulation device 60. The articulation is presented below with reference to FIG. 7.

In the straight working angular position 75 of the distal part 62 of the articulation device 60 shown in FIG. 4, the lobe 88 on the slide 84 abuts on the proximal part 61 of the articulation device 60 or is arranged at a short distance therefrom. In the angled working angular position 74 of the distal part 62 of the articulation device 60 shown in FIG. 5, the lobe 88 on the slide 84 is distanced from the proximal part 61 of the articulation device. In both cases, the slide 84 adopts its most proximal position due to the effect of the spring 83. In this most proximal position of the slide 84, the bolts 85 adopt their locking positions already described above with reference to FIG. 4, wherein each bolt 85 protrudes in part into the circumferential portion 82 of one of the L-shaped grooves.

Figure 6:
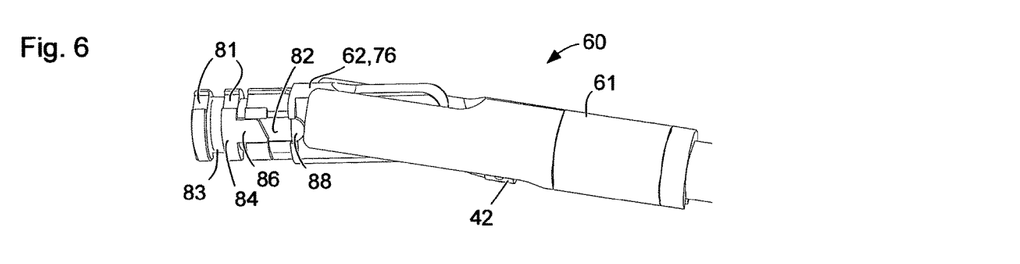
FIG. 6 shows a further schematic axonometric illustration of the articulation device from FIGS. 4 and 5.

FIG. 6 shows a further schematic axonometric illustration of the articulation device 6 from FIGS. 4 and 5. The illustration in FIG. 6 differs from the illustrations in FIGS. 4 and 5 in that the articulation device, in particular the distal part 62 of the articulation device 60, adopts a release angular position 76. Based on the straight working angular position 75 shown in FIG. 4, the release angular position 76 of the angled working angular position 74 shown in FIG. 5 is arranged opposite. In other words, the straight working angular position 75 shown in FIG. 4 is arranged between the angled working angular position 74 shown in FIG. 5 and the release angular position 76 shown in FIG. 6.

Due to the arrangement of the pivot axis 68 (see FIG. 1) at a distance from the straight line over which the lobes 88 are movable, the lobes 88 in the release angular position 76 of the distal part 62 of the articulation device 60 abut on a distal end face of the proximal part 61 of the articulation device, and the slide 84 is displaced into a distal position against the force of the spring 83. In this distal position of the slide 84, the bolts adopt unlocking positions 86. In the unlocking position 86, the bolts do not protrude into the circumferential portion 82 of the L-shaped groove on the coupling 80. Catches 25 of a tool 20 (see FIGS. 2 and 3) can therefore be freely moved in the circumferential portions 82 and therefore in the L-shaped grooves as a whole. In the release angular position of the distal part 62 of the articulation device 60 shown in FIG. 6, a mechanical connection between a tool 20 and the articulation device 60 can therefore be released or cancelled or separated.

In FIG. 6, a part of a distal end 42 of an inner shaft 40 (see FIG. 1) can be seen, of which the function is described in greater detail below with reference to FIGS. 8 and 11 to 13.

Figure 7:
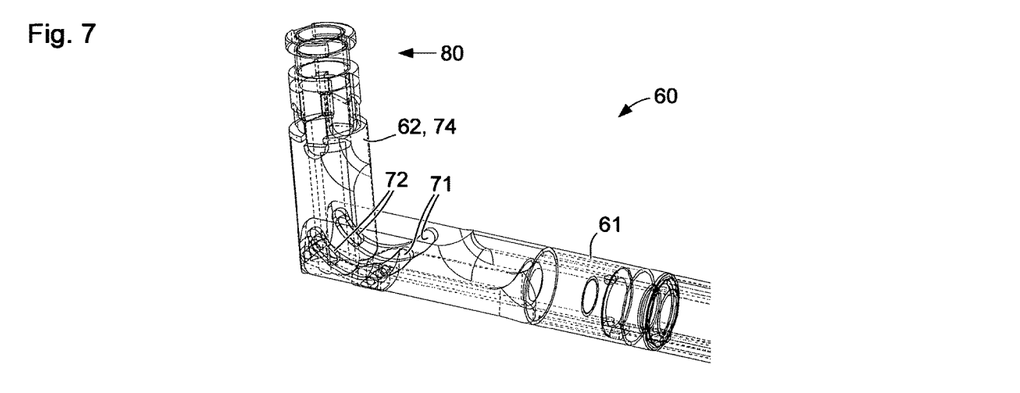
FIG. 7 shows a further schematic axonometric illustration of the articulation device from FIGS. 4 to 6.

FIG. 7 shows a further schematic axonometric illustration of the articulation device 60 from FIGS. 4 to 6. The illustration in FIG. 7 corresponds to FIG. 5, in particular with regard to the shown working angular position 74 of the distal part 62 of the articulation device 60 and with regard to the perspective or the viewer position. The illustration in FIG. 7 differs from the illustration in FIG. 5 in particular in that all elements or components of the articulation device 60 are illustrated transparently. Visible contours, borders, edges and boundaries between surfaces of different curvature are illustrated by solid lines, and those that are not visible are illustrated by dashed lines.

In FIG. 7, the grooves 71 shaped in the manner of a circular arc and already mentioned above on the inner faces of the distal ends of the fork-shaped proximal part 61 of the articulation device 60 can be seen. Furthermore, webs 72 on the outer faces of the distal part 62 of the articulation device 60 can be seen and each engage into a respective one of the grooves 71. The curved grooves 71 and the webs 72 form the actual articulation of the articulation device 60. The centers of curvature of the sliding faces bearing against one another in the grooves 71 and bearing against the webs 72 define the position and orientation of the pivot axis.

Figure 8:
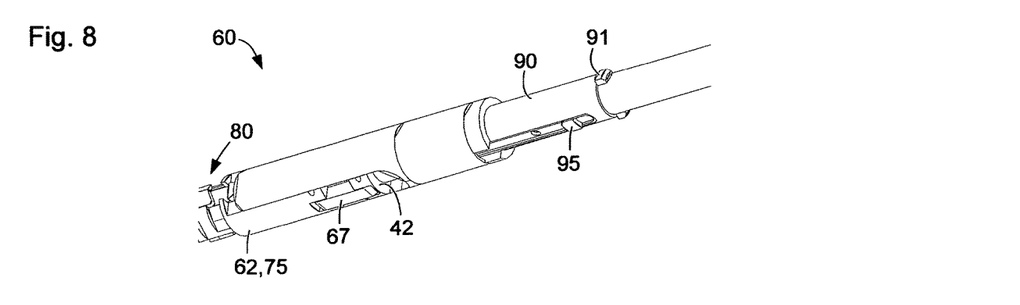
FIG. 8 shows a further schematic axonometric illustration of the articulation device from FIGS. 4 to 7.

FIG. 8 shows a further schematic axonometric illustration of the articulation device from FIGS. 4 to 7. The illustration in FIG. 8 corresponds to the illustration in FIG. 4 with respect to the shown working angular position 75 of the distal part 62 of the articulation device 60. The illustration in FIG. 8 differs from the illustration in FIG. 4 by a different perspective or a different viewer position. In particular, a slightly larger part of the distal end 42 of the inner shaft 40 also visible in part in FIG. 6 can be seen. The elbowed distal end 42 of the inner shaft 40 is coupled or articulated by means of a connecting rod 76 to the distal part 62 of the articulation device 60. An axial movement or a movement in translation of the inner shaft 40 parallel with respect to the longitudinal axis 38 (see FIG. 1) is coupled by means of the connecting rod 67 to a pivoting movement of the distal part 62 of the articulation device 60.

In FIG. 8, a shaft coupling 90 at the proximal end of the proximal part 61 of the articulation device 60 can also be seen. The shaft coupling 90 comprises at a proximal edge of a tubular portion two mutually opposed, radially outwardly protruding claws or catches 91. Furthermore, a bolt, which is shown in FIG. 8 in a locking position 95, is displaceable in an axial slit in the shaft coupling 90. The bolt 95 is in particular connected rigidly to the inner shaft 40 and is displaceable together therewith in the axial direction.

Figure 9:
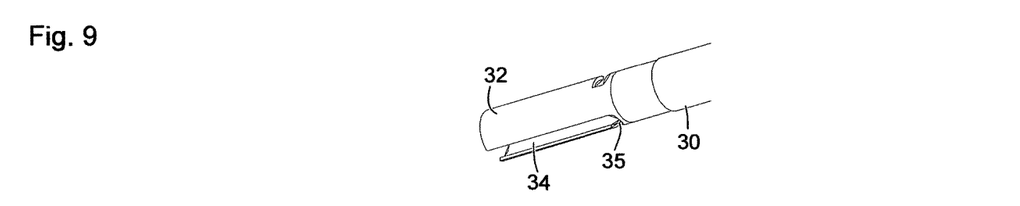
FIG. 9 shows a schematic axonometric illustration of a distal end of a shaft.

FIG. 9 shows a schematic axonometric illustration of a distal end 32 of an outer shaft 30. The distal end 32 of the outer shaft 30 is formed as a bayonet coupling comprising two mutually opposed L-shaped slits. One of the two L-shaped slits is largely visible in FIG. 9, and only part of the proximal end of the other L-shaped slit can be seen. Each L-shaped slit comprises an axial portion 34 and, at its proximal end, a circumferential portion 35. The L-shaped slits 34, 35 are arranged and designed such that they can each receive a catch 91 on the shaft coupling 90 at the proximal end of an articulation device 60 (see FIG. 8) and a bolt 95.

Figure 10:
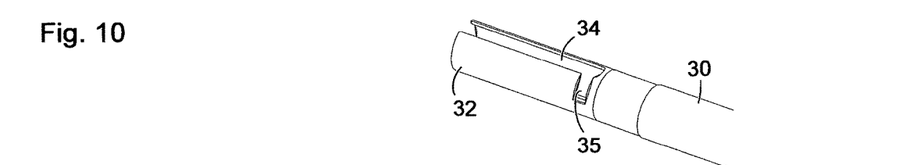
FIG. 10 shows a further schematic axonometric illustration of the distal end of a shaft from FIG. 9.

FIG. 10 shows a further schematic axonometric illustration of the distal end 32 of the outer shaft 30 from FIG. 9. The illustration in FIG. 10 differs from the illustration in FIG. 9 by a different perspective or a different viewer position.

Initially disregarding the action of the bolt 95 (see FIG. 8), the catches 91 at the proximal end of the articulation device 60 can, after introduction of the inner shaft 40 into the outer shaft 30, be introduced by means of an axial movement from the distal direction in the proximal direction into the axial portions 34 of the L-shaped slit at the distal end 32 of the outer shaft 30. When the catches 91 have reached the proximal ends of the axial portions 34 of the L-shaped slits, they can be introduced into the circumferential portions 35 of the L-shaped slits as a result of a rotation of the articulation device 60 relative to the outer shaft 30 about the longitudinal axis 38 (see FIG. 1).

When the catches 91 are located in the circumferential portions 35 of the L-shaped slits, and when the bolt 95 is located in the position shown in FIG. 8, the bolts 95 on the shaft coupling 90 at the proximal end of the articulation device 60 engage into the axial portions 34 of the L-shaped slits. A rotation of the articulation device 60 relative to the outer shaft 30 is thus prevented, and the catches 91 on the articulation device 60 are held in the circumferential portions 35 of the L-shaped slits at the distal end 32 of the outer shaft 30, thus locking the rigid mechanical connection between the articulation device 60 and outer shaft 30.

By contrast with the illustrations in FIGS. 9 and 10, the distal end 32 of the outer shaft 30 may be surrounded by a thin-walled circular-cylindrical-shaped protective sleeve.

Figure 11:
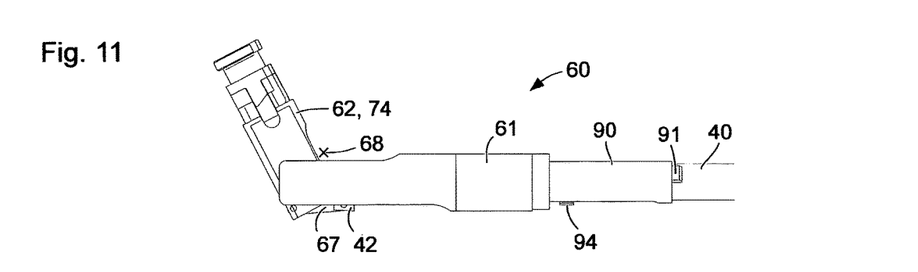
FIG. 11 shows a further schematic illustration of the articulation device from FIGS. 4 to 8.
Figure 12:
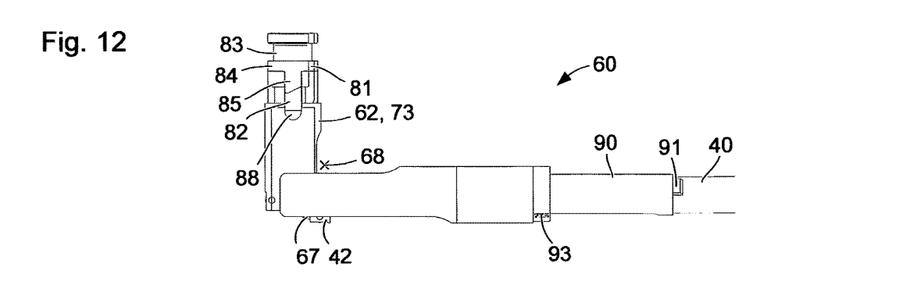
FIG. 12 shows a further schematic illustration of the articulation device from FIGS. 4 to 8 and 11.
Figure 13:
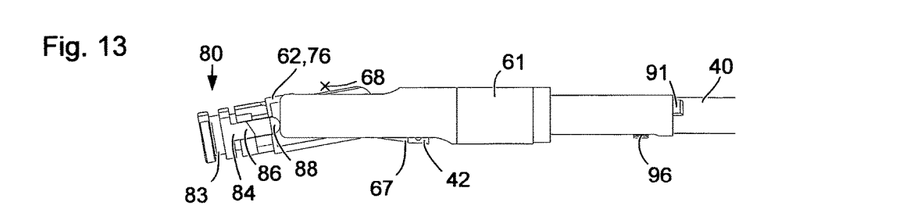
FIG. 13 shows a further schematic illustration of the articulation device from FIGS. 4 to 8, 11 and 12.

FIGS. 11 to 13 show further schematic illustrations of the articulation device 60 from FIGS. 4 to 8. In FIGS. 11 to 13, the distal end 42 of the inner shaft 40 and of the connecting rod 67, which couples the distal end 42 of the inner shaft 40 to the distal part 62 of the articulation device 60, are each visible in part.

In FIGS. 11 to 13, it can be seen that different axial-translatory positions of the inner shaft 40 or of the distal end 42 thereof correspond to different angular positions 73, 74, 76 of the distal part 62 of the articulation device 60. It can also be seen that, due to a rigid coupling to the inner shaft 40, different positions 93, 94, 96 of the bolt on the shaft coupling 90 correspond to the angular positions 73, 74, 76 of the distal part 62 of the articulation device 60.

In the angular position 73 of the distal part 62 of the articulation device 60 angled at right angles and shown in FIG. 12, the bolt adopts an unlocking position 93 in the proximal end of the articulation device 61, in which it cannot engage into an axial portion 34 of an L-shaped slit at the distal end 32 of an outer shaft 30 (see FIGS. 9 and 10). The angular position 73 shown in FIG. 12 of the distal part 62 of the articulation device 60 is therefore a release angular position with regard to a mechanical connection of the articulation device 60 to a distal end 32 of an outer shaft 30 by means of the shaft coupling 90.

With regard to the mechanical connection of the articulation device 60 to a tool 20 (see FIGS. 2 and 3) by means of the coupling 80, the angular position 76 shown in FIG. 13 of the distal part 62 of the articulation device 60 is by contrast a release angular position.

Symmetrically with respect to the bolt 93, 94, 95, 96 visible in FIGS. 8 and 11 to 13, a further bolt can be provided in a further slit.

REFERENCE SIGNS 10 medical instrument
11 proximal end of the medical instrument 10
12 distal end of the medical instrument 10
14 handling device at the proximal end 11 of the medical instrument 10
20 tool
21 proximal end of the tool 20
22 stationary mouth part of the tool 20
23 pivotable mouth part of the tool 20
25 catch at the proximal end 21 of the tool 20
26 sleeve at the proximal end 21 of the tool 20
28 axis of rotation of the tool 20
30 outer shaft
31 proximal end of the outer shaft 30
32 distal end of the outer shaft 30
34 axial portion of a slit at the distal end 32 of the outer shaft 30
35 circumferential portion of a slit at the distal end 32 of the outer shaft 30
38 longitudinal axis of the outer shaft 30
40 inner shaft
50 transfer rod
51 rigid proximal portion of the transfer rod 50
52 resilient distal portion of the transfer rod 50
60 articulation device
61 proximal part of the articulation device 60
62 distal part of the articulation device 60
67 connecting rod
68 pivot axis of the articulation device 60
71 groove on the proximal part 61 of the articulation device 60
72 web on the distal part 62 of the articulation device 60
73 release angular position of the distal part 62 of the articulation device 60
74 first working angular position of the distal part 62 of the articulation device 60
75 second working angular position of the distal part 62 of the articulation device 60
76 third working angular position of the distal part 62 of the articulation device 60
80 coupling at the distal end 62 of the articulation device 60
81 axial portion of a groove on the coupling 80
82 circumferential portion of a groove on the coupling 80
83 spring
84 slide on the coupling 80
85 bolt on the slide 84 in locking position
86 bolt on the slide 84 in unlocking position
87 web between bolts 85, 86 and lobe 88
88 lobe on the slide 84
90 coupling at the proximal end 61 of the articulation device 60
91 catch on the coupling 90
93 bolt on the coupling 90 (unlocking position)
94 bolt on the coupling 90 (first locking position)
95 bolt on the coupling 90 (second locking position)
96 bolt on the coupling 90 (third locking position)

The invention claimed is:
1. A medical instrument, comprising:
a shaft extending along a longitudinal axis between a proximal end and a distal end of the shaft;
an articulation having a proximal portion and a distal portion;
the proximal portion of the articulation connected to the distal end of the shaft, the proximal portion being fork-shaped and including a first groove formed on a first inner face of a first distal end of the proximal portion and a second groove formed on a second inner face of a second distal end of the proximal portion;
the distal portion of the articulation releasably connected to a tool, the distal portion including a first web on a first outer face of the distal portion and a second web on a second outer face of the distal portion, the first web and the second web of the distal portion engaging the first groove and the second groove of the proximal portion, respectively, such that the distal portion is pivotable relative to the proximal portion about a pivot axis between a first working angular position, a second working angular position, and a releasing angular position, wherein the pivot axis is not parallel with respect to the longitudinal axis of the shaft; and
a lock configured to maintain a connection between the distal portion of the articulation and the tool during pivoting of the distal portion between the first working angular position and the second working angular position, and configured to release the connection between the distal portion of the articulation and the tool when the distal portion of the articulation is in the releasing angular position;

wherein the lock is configured to maintain the connection between the distal portion of the articulation and the tool when the distal portion is in the first working angular position, and when the distal portion is in the second working angular position;

wherein the lock includes a bolt movable in a direction of the longitudinal axis of the shaft between a predetermined locking position and a predetermined unlocking position;

wherein in the predetermined locking position of the bolt, the lock maintains the connection between the distal portion of the articulation and the tool; and wherein in the predetermined unlocking position of the bolt, the lock releases the connection between the distal portion of the articulation and the tool.

2. The medical instrument of claim 1, wherein the pivot axis is perpendicular to the longitudinal axis of the shaft.

3. The medical instrument of claim 1, wherein the pivot axis is substantially perpendicular to the longitudinal axis of the shaft.

4. The medical instrument of claim 1, wherein the pivot axis is at an angle of at least 60 degrees to the longitudinal axis of the shaft.

5. The medical instrument of claim 1, wherein the pivot axis is at an angle of at least 80 degrees to the longitudinal axis of the shaft.

6. The medical instrument of claim 1, wherein a longitudinal axis of the distal portion of the articulation is at a first angle relative to the longitudinal axis of the shaft when the distal portion is in the first working angular position;

wherein the longitudinal axis of the distal portion of the articulation is at a second angle relative to the longitudinal axis of the shaft when the distal portion is in the second working angular position;

wherein the longitudinal axis of the distal portion of the articulation is at a third angle relative to the longitudinal axis of the shaft when the distal portion is in the releasing angular position; and wherein the first angle, the second angle, and the third angle are different relative to one another.

7. The medical instrument of claim 1, wherein the distal portion of the articulation includes a groove configured to receive a catch at a proximal end of the tool.

8. The medical instrument of claim 1, wherein the proximal portion of the articulation is releasably connected to the distal end of the shaft; and wherein the medical instrument further comprises a shaft lock configured to maintain the connection between the proximal portion of the articulation and the distal end of the shaft.

9. The medical instrument of claim 8, wherein the shaft lock is configured to release the connection between the proximal portion of the articulation and the distal end of the shaft when the distal portion of the articulation is in the releasing angular position.

10. The medical instrument of claim 9, further comprising a transfer device coupled to the articulation, the transfer device configured to transfer a force from a proximal end of the medical instrument to the articulation, and the transfer device configured to adjust an angular position of the articulation from the proximal end of the medical instrument; and wherein the shaft lock is coupled to the transfer device.

11. The medical instrument of claim 1, wherein the pivot axis does not intersect the articulation.

12. The medical instrument of claim 1, wherein the first groove is a first circular arc groove and the second groove is a second circular arc groove.

13. A medical instrument, comprising:
a shaft extending along a longitudinal axis between a proximal end and a distal end of the shaft;
an articulation having a proximal portion and a distal portion;
the proximal portion of the articulation connected to the distal end of the shaft, the proximal portion being fork-shaped and including a first groove formed on a first inner face of a first distal end of the proximal portion and a second groove formed on a second inner face of a second distal end of the proximal portion;
the distal portion of the articulation releasably connected to a tool, the distal portion including a first web on a first outer face of the distal portion and a second web on a second outer face of the distal portion, the first web and the second web of the distal portion engaging the first groove and the second groove of the proximal portion, respectively, such that the distal portion is pivotable relative to the proximal portion about a pivot axis between a first working angular position, a second working angular position, and a releasing angular position, wherein the pivot axis is not parallel with respect to the longitudinal axis of the shaft; and
a lock configured to maintain a connection between the distal portion of the articulation and the tool during pivoting of the distal portion between the first working angular position and the second working angular position, and configured to release the connection between the distal portion of the articulation and the tool when the distal portion of the articulation is in the releasing angular position;
wherein the lock is configured to maintain the connection between the distal portion of the articulation and the tool when the distal portion is in the first working angular position, and when the distal portion is in the second working angular position;
wherein the lock includes a bolt movable in a direction of the longitudinal axis of the shaft between a predetermined locking position and a predetermined unlocking position;
wherein in the predetermined locking position of the bolt, the lock maintains the connection between the distal portion of the articulation and the tool;
wherein in the predetermined unlocking position of the bolt, the lock releases the connection between the distal portion of the articulation and the tool;
wherein the bolt is guided on the distal portion of the articulation; and
wherein the bolt abuts against the proximal portion of the articulation when the distal portion of the articulation is in the releasing angular position.

14. A medical instrument, comprising:
a shaft extending along a longitudinal axis between a proximal end and a distal end of the shaft;
an articulation having a proximal portion and a distal portion;
the proximal portion of the articulation connected to the distal end of the shaft, the proximal portion being fork-shaped and including a first groove formed on a first inner face of a first distal end of the proximal portion and a second groove formed on a second inner face of a second distal end of the proximal portion;

the distal portion of the articulation releasably connected to a tool, the distal portion including a first web on a first outer face of the distal portion and a second web on a second outer face of the distal portion, the first web and the second web of the distal portion engaging the first groove and the second groove of the proximal portion, respectively, such that the distal portion is pivotable relative to the proximal portion about a pivot axis between a first working angular position, a second working angular position, and a releasing angular position, wherein the pivot axis is not parallel with respect to the longitudinal axis of the shaft;

a lock configured to maintain a connection between the distal portion of the articulation and the tool during pivoting of the distal portion between the first working angular position and the second working angular position, and configured to release the connection between the distal portion of the articulation and the tool when the distal portion of the articulation is in the releasing angular position; and a handle configured to be releasably mechanically coupled to the proximal end of the shaft, wherein the releasing angular position of the distal portion of the articulation cannot be reached when the handle is coupled to the proximal end of the shaft.

15. The medical instrument of claim 14, wherein the pivot axis is at an angle of at least 60 degrees to the longitudinal axis of the shaft.

16. The medical instrument of claim 14, wherein the pivot axis does not intersect the articulation.

17. The medical instrument of claim 14, wherein a longitudinal axis of the distal portion of the articulation is at a first angle relative to the longitudinal axis of the shaft when the distal portion is in the first working angular position;

wherein the longitudinal axis of the distal portion of the articulation is at a second angle relative to the longitudinal axis of the shaft when the distal portion is in the second working angular position;

wherein the longitudinal axis of the distal portion of the articulation is at a third angle relative to the longitudinal axis of the shaft when the distal portion is in the releasing angular position; and wherein the first angle, the second angle, and the third angle are different relative to one another.

18. The medical instrument of claim 14, wherein the lock is configured to maintain the connection between the distal portion of the articulation and the tool when the distal portion is in the first working angular position, and when the distal portion is in the second working angular position.

19. The medical instrument of claim 14, wherein the distal portion of the articulation includes a groove configured to receive a catch at a proximal end of the tool.

20. The medical instrument of claim 14, wherein the proximal portion of the articulation is releasably connected to the distal end of the shaft;

wherein the medical instrument further comprises a shaft lock configured to maintain the connection between the proximal portion of the articulation and the distal end of the shaft; and wherein the shaft lock is configured to release the connection between the proximal portion of the articulation and the distal end of the shaft when the distal portion of the articulation is in the releasing angular position.

* * * * *